United States Patent [19]

Imahashi et al.

[11] Patent Number: 5,374,327
[45] Date of Patent: Dec. 20, 1994

[54] PLASMA PROCESSING METHOD

[75] Inventors: Issei Imahashi; Nobuo Ishii; Chishio Koshimizu, all of Yamanashi, Japan

[73] Assignee: Tokyo Electron Limited, Tokyo, Japan

[21] Appl. No.: 53,353

[22] Filed: Apr. 28, 1993

[30] Foreign Application Priority Data

Apr. 28, 1992 [JP] Japan .................. 4-135881

[51] Int. Cl.$^5$ ............................. G01N 21/00
[52] U.S. Cl. ........................ 156/626; 156/643
[58] Field of Search .............. 156/626, 627, 643; 204/192.33, 192.13, 298.03, 298.32; 427/8-10, 571, 575

[56] References Cited

U.S. PATENT DOCUMENTS

| 4,289,188 | 9/1981 | Mizutani et al. | 156/626 |
| 4,430,151 | 2/1984 | Tsukada | 156/626 |
| 4,704,199 | 11/1987 | Yokokawa et al. | 204/298.03 |

FOREIGN PATENT DOCUMENTS

| 56-133466 | 10/1981 | Japan . | |
| 57-12529 | 3/1982 | Japan . | |
| 220332 | 9/1986 | Japan | 156/345 |
| 63-81929 | 4/1988 | Japan . | |
| 25418 | 1/1989 | Japan | 156/626 |
| 48419 | 2/1989 | Japan | 156/626 |
| 175740 | 7/1989 | Japan | 156/626 |
| 35723 | 2/1990 | Japan | 156/626 |
| 26781 | 1/1992 | Japan | 204/298.32 |

*Primary Examiner*—Thi Dang
*Attorney, Agent, or Firm*—Oblon, Spivak, McClelland, Maier & Neustadt

[57] ABSTRACT

HBr and Cl$_2$ are used as etching gases and Ar is used as a carrier gas in an ECR etching apparatus in which a semiconductor wafer is processed. Light emitted from plasma generated is dispersed by first and second spectroscopes to detect intensities of those spectra of the plasma which have first and second wavelengths. Both of these spectra are selected from those of an Ar atom. A CPU compares a present value, which represents a ratio of the spectral intensities detected, with a selected value of the ratio previously stored, and adjusts the intensity of a magnetic field such that the present value becomes closer to the selected value. The adjustment of the magnetic field intensity is carried out by changing the value of a current applied to magnetic coils. The magnetic field intensity is a parameter for adjusting an electron temperature of the plasma, and thus, the electron temperature of the plasma is adjusted by adjusting the magnetic field intensity.

18 Claims, 5 Drawing Sheets

PLASMA PROCESSING METHOD

BACKGROUND OF THE INVENTION

1. Field of the Invention

The present invention relates to a plasma processing method and, more particularly, a method of keeping plasma under a predetermined state or changing it to the predetermined state on the basis of spectral strengths of its emission light.

2. Description of the Related Art

When a plurality of objects such as semiconductor wafers are successively etching-processed at the same process in the plasma etching apparatus, for example, plasma generating parameters such as RF power, the vacuum degree in a process chamber and flow rates of processing gases are set constant. Even if these parameters are set constant for this etching apparatus, however, practical etching conditions change as time goes by. This is because conditions in the process chamber are changed by by-products such as a film deposited in the chamber as time goes by.

The process chamber must be therefore periodically cleaned, and when the process which is applied to the wafers becomes more precise, the process chamber must be more frequently cleaned. Even if the process chamber is cleaned in this manner, conditions in it just after it is cleaned become different from those in it just before it is cleaned. Even if values of the parameters are made constant, therefore, the state of plasma is changed every etching process by those conditions in the chamber which change as time goes by. This sets a limit to that the precise process can be uniformly applied to every object to be processed.

Further, the state of plasma is sometimes changed even in one time etching process by fluctuation of the frequency of RF power source or the composition of gas, or temperature rise of an electrode or the chamber wall.

As described above, the state of plasma is changed every etching process and every time plural different processes are conducted in the chamber. When the state of plasma is changed in this manner, it becomes difficult to produce semiconductor devices, such as memories of 64M, 256M and more, which require a precise process. Recently, the semiconductors have been more and more highly microstructured. Therefore, the state of plasma must be more precisely controlled.

The state of plasma has been monitored to detect the end point of the etching process. The emission light spectral intensity of a specific wavelength in the plasma is detected in this case. This specific wavelength is selected from wavelengths whose spectral intensity varies depending on the progress of the etching process, and is generally an emission light wavelength of one of those atoms and molecules which form the object etched and the product generated in the etching process. Emission light spectral intensities of plural specific wavelengths are also detected to prevent the end point of the etching process from being wrongly detected because of the drift of plasma. These teachings are disclosed by Published Examined Japanese Patent Application No. 57-12529 and Published Unexamined Japanese patent Application No. 56-133466, for example.

However, it has not been conducted that the state of plasma is controlled while monitor it. Values of parameters, which determine the state of plasma, are kept constant during a plasma process.

SUMMARY OF THE INVENTION

The object of the present invention is therefore to provide a method of monitoring the emission light of plasma and feeding results thus monitored back to the plasma control to keep and change the state of plasma as desired.

According to the present invention, there is provided a method of generating plasma to process a substrate with the plasma in a process chamber, comprising the steps of: selecting plasma to be generated in the chamber and raw gas to generate the selected plasma; selecting a first parameter which is one of conditions of generating the selected plasma, electron temperature or electron density of the selected plasma being changeable by changing the first parameter; forming a formula using, as functions, intensities of spectra having first and second wavelengths in emission light of the selected plasma, and establishing, as first datum, relation between the formula and the electron temperature or electron density of the selected plasma; establishing, as second datum, relation between the electron temperature or electron density of the selected plasma and the first parameter; establishing, as third datum, relation between the formula and the first parameter from the first data, and storing the third datum in a memory of a control unit; storing a selected value of the formula in the memory of the control unit; loading the substrate into the chamber; setting the chamber to have a vacuum atmosphere; introducing the selected raw gas into the chamber while exhausting the chamber; generating plasma by making the raw gas into plasma; guiding light emitted from the generated plasma into first and second spectroscopes; detecting intensities of spectra having the first and second wavelengths in the emitted light by the spectroscopes; calculating present value of the formula in the generated plasma from the detected spectral intensities by means of the control unit; adjusting the first parameter by the control unit, while monitoring the present value, such that the present value becomes closer to the selected value; and processing the substrate with the generated plasma.

According to the present invention, those spectral intensities in the emitted light of plasma which have plural different wavelengths are dispersed. Each spectral intensity changes depending upon the state of plasma. Plasma temperature, for example, can be cited as an indication for representing the state of plasma. This plasma temperature denotes the total sum of electron, ion and radical temperatures and particularly the average electron temperature is closely related to the spectral intensities of the emitted light of plasma. To cite an example of this, the intensity of spectrum having a relatively short wavelength becomes large when the average electron temperature is high and it becomes small when the average electron temperature is low. On the other hand, the intensity of spectrum having a relatively long wavelength becomes small when the average electron temperature is high and it becomes large when the average electron temperature is low.

If only the spectral intensity of a specific wavelength is monitored, wrong control is caused by those influences of noises and variations which are added to the whole of background. When spectral intensities of plural different wavelengths are monitored, however, it can be understood that the plasma temperature changes as the correlation of these spectral intensities, such as ratio thereof, changes. This makes it possible to correctly monitor the state of plasma. When at least one of those parameters which are used to generate plasma is controlled on the basis of the correlation, the state of plasma can be controlled certain or changed as desired.

It is preferable that each of the spectra of different wavelengths represents an atom or molecule which contributes nothing to the progress of etching process or neither substantially nor chemically acts on the substrate. This enable the state of plasma to be more stably controlled.

When plasma is generated using the electron cyclotron resonance phenomenon, it is easier to control the state of plasma while changing the intensity of magnetic field.

When plasma is generated between parallel plate electrodes, the state of plasma can be effectively controlled by changing the vacuum degree of plasma processing atmosphere or the gas pressure in the process chamber.

Further, the plasma temperature, particular the average electron temperature is closely related to amounts of ions and radicals generated.

When the average electron temperature is relatively high, for example, the amount of ions generated becomes larger than that of radicals generated. When it becomes low, the amount of ions generated becomes smaller than that of radicals generated. When at least one of those parameters which are used to generate plasma is controlled on the basis of the correlation between spectral intensities of plural different wavelengths to change the plasma temperature, therefore, the ratio of ions and radicals generated can be changed.

According to the present invention, spectral intensities in the emission light of plasma which have different wavelengths are monitored and result thus monitored are fed back to the plasma control to keep the state of plasma substantially certain or to change it as desired. A more uniform and correct plasma process can be thus achieved without being adversely affected by any uncertain condition in the process chamber.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

A first embodiment of the present invention will be described in detail with reference to the accompanying drawings. In the case of this first embodiment, the present invention will be applied to the apparatus which is intended to carry out plasma etching using electron cyclotron resonance (ECR).

Figure 1:
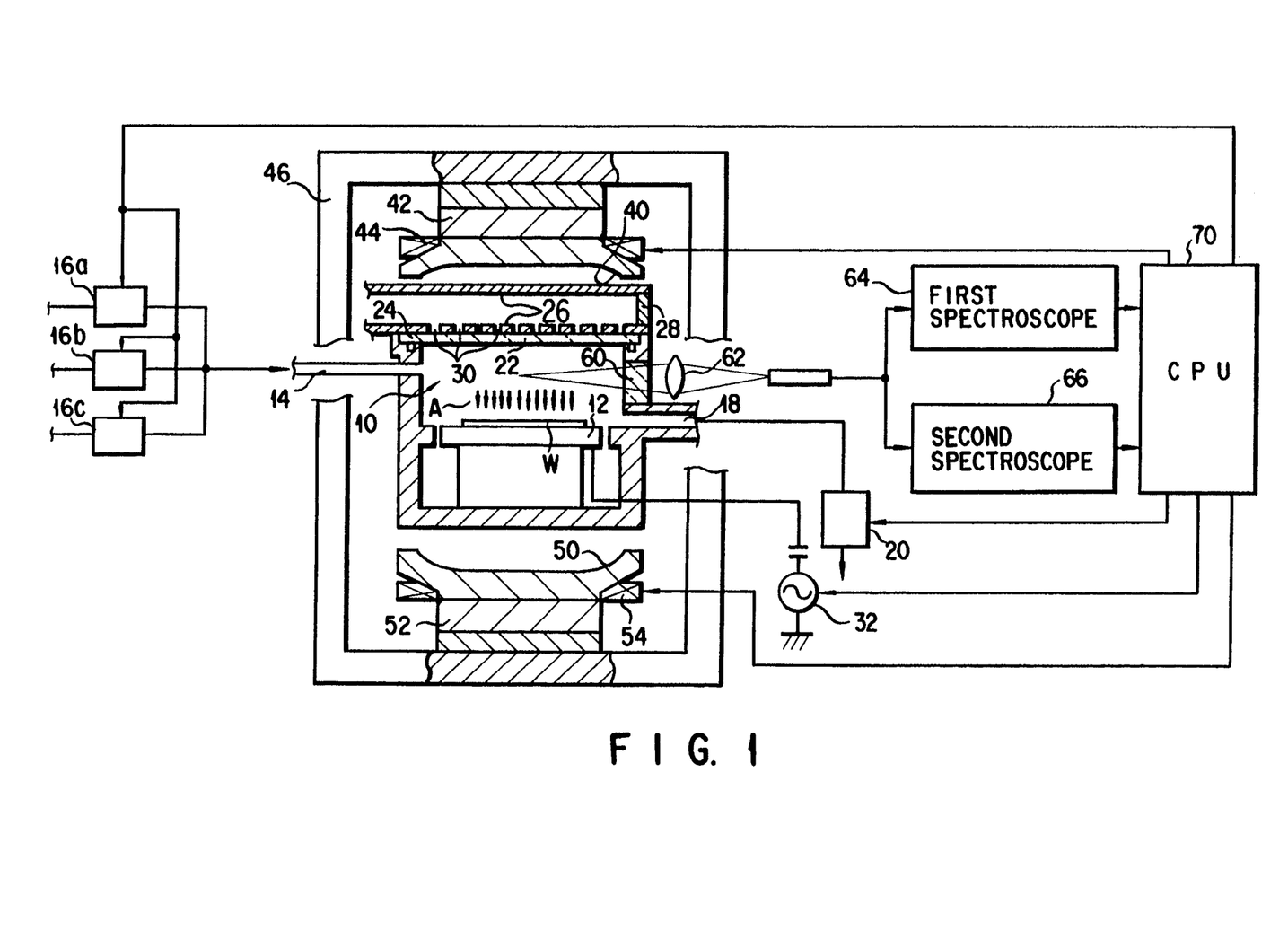
FIG. 1 schematically shows an ECR etching apparatus according to a first embodiment of the present invention.

In FIG. 1, a process chamber 10 provides a discharge space in which plasma is generated by electron cyclotron resonance. It is shaped like a cylinder having a diameter of 600 mm, for example, and its side wall is made of aluminium alloy or stainless steel. A conductive table 12 is arranged in it to support a semiconductor wafer W which is to be processed. An RF power source 32 is connected to the table 12.

A gas pipe 14 is connected to the chamber 10 to introduce process gases into the chamber 10. Three kinds of gases, such as HBr and $Cl_2$ which are used as etching gases and Ar which is used as carrier gas, can be introduced into the chamber 10 through the gas pipe 14 in the case of this embodiment and mass flow controllers 16a–16c are provided to adjust flow rates of these three gases. The chamber 10 can be kept to have a vacuum atmosphere of $5 \times 10^{-4}$ Torr. To keep the chamber 10 under this vacuum atmosphere, an exhaust pipe 18, which is connected to an exhaust pump (not shown) at its one end, is connected to the chamber 10 at its other end. A pressure controller 20 is connected halfway the exhaust pipe 18 to adjust the pressure of gas exhausted. A window 22 made of quartz glass to allow microwave to pass through is attached to the top of the chamber 10 through an O-ring 24.

A hollow rectangular waveguide 26 is arranged above the chamber 10. It is connected to a microwave supply source (not shown) to guide a microwave of 2.45 GHz, for example, above the chamber 10. Its front end bottom is provided with a plurality of slit-like microwave openings 30, which are faced the window 22. The slit width of each opening 30 is $\lambda t/2$ cm ($\lambda t$ represents the wavelength of the microwave in the waveguide 26). The front end face of the waveguide 26 is formed by a microwave absorber 28, which absorbs wave reflected in the waveguide 26 not to return back to the microwave supply source. The absorber 28 is cooled not to heat the waveguide 26.

The area between the microwave openings 30 and the top of the support 12 serves as a cavity in which microwave resonates. The height or distance of this area is set ($\lambda g/2$)×n (n represents an integer) or ($\lambda g/2$)×2, for example, providing that the wavelength of the microwave introduced into the chamber 10 through the microwave openings 30 is $\lambda g$. An upper magnetic pole 40 is arranged outside the waveguide 26 and above the chamber 10. A lower magnetic pole 50 is also arranged under the chamber 10. These upper and lower magnetic poles 40 and 50 are magnetically connected to each other through permanent magnets 42 and 52 by a soft-iron-made yoke 46. Further, magnetic field generating coils 44 and 54 are wound round their corresponding magnetic poles 40 and 50. Magnetic field generating means is formed in this case by these magnetic poles 40, permanent magnets 42, 52, coils 44, 54 and yoke 46 and it serves to generate in the chamber 10 a magnetic field which has a certain magnetic flux density and whose magnetic lines A are directed from above to down and perpendicular to the semiconductor wafer W.

According to the above-described apparatus, microwave having a power of 800 W and a frequency of 2.45 GHz is propagated from the microwave supply source into the waveguide 26 and introduced into the chamber under TE (transverse electric) mode through the microwave openings 30 and the window 22. Further, a magnetic field which has a magnetic flux density of 875 gausses, for example, and whose magnetic lines A are directed from above to down and perpendicular to the wafer W on the table 12 is generated in the chamber 10 while exciting the permanent magnets 42, 52 and the coils 44, 54. Still further, introducing HBr, $Cl_2$ and Ar into the chamber 10 through the gas pipe 14 at predetermined flow rates while exhausting the chamber 10 through the exhaust pipe 18, the pressure in the chamber 10 is kept about $5 \times 10^{-4}$ Torr, for example. The wafer W is thus etched.

In order to monitor the state of plasma generated in the chamber 10, a detection window 60 made of quartz, for example, is formed in the side wall of the chamber 10. The light of plasma taken outside the chamber 10 through the window 60 is collected through lens 62 and entered into first and second spectroscopes 64 and 66, which measure intensities of spectra independent of the etching progress, such as spectra of two different wavelengths of Ar, respectively. A CPU 70 to which outputs are applied from the first and second spectroscopes 64 and 66 controls the state of plasma in the chamber 10, responsive to the correlation of outputs thus applied from the first and second spectroscopes 64 and 66.

When the above-described apparatus is to be used, wafer W is mounted on the table 12 in the chamber 10 and the chamber 10 is made to have a predetermined vacuum atmosphere of $5 \times 10^{-4}$ Torr, for example. Etching gases such as HBr and $Cl_2$ are introduced together with carrier gas such as Ar into the chamber 10 while exhausting the chamber 10. When RF power is added to the table 12 and microwave is supplied into the chamber 10 under this state, the gases are made into plasma. The wafer on the table 12 is etched by the chemical action of radicals of etching gas atoms in the plasma and by the physical action of ions in the plasma.

According to the present invention, the light emitted from plasma is dispersed during etching of the wafer, and the state of plasma is controlled as described below. The ratio of flow rates of gases introduced, vacuum degree of the chamber 10, RF power supplied and the intensity of magnetic field can be cited as parameters for controlling the state of plasma. The CPU 70 is connected to the mass flow controllers 16a–16c, the pressure controller 20, the RF power source 32 and the coils 44, 54 so as to control these parameters.

A case where parameters except intensity of magnetic field are made constant and the CPU 70 changes coil current, which is applied to the coils 44 and 54, responsive to outputs of the first and second spectroscopes 64 and 66 will be described.

Figure 7:
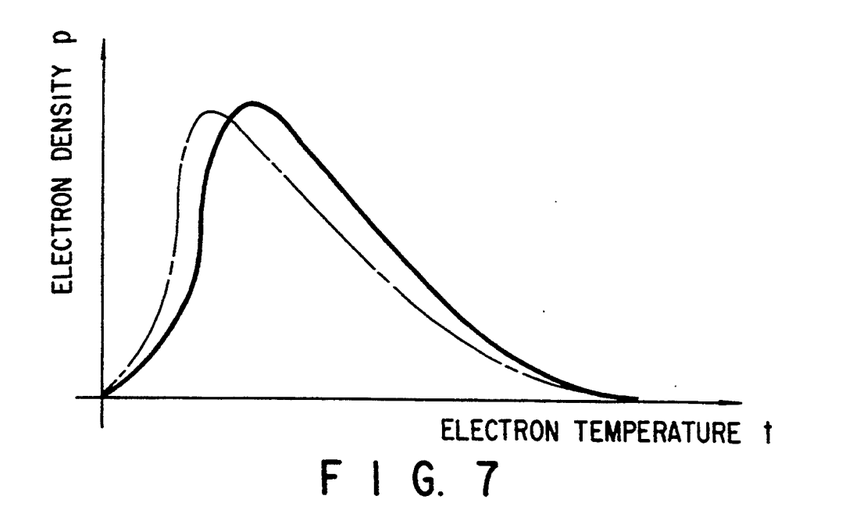
FIG. 7 is a characteristic view showing distributions of electron densities relative to electron temperature.

Inventors of the present invention paid their attention at first to electron temperature, which is an element for determining the state of plasma. In FIG. 7, the abscissa represents electron temperatures t while the ordinate densities p of electrons present. In short, FIG. 7 shows distributions of electron densities relative to electron temperatures t. As apparent from FIG. 7, they are Boltzmann distributions. A distribution of electron densities shown by a dot- and dash-line has temperatures lower than those of another distribution shown by a solid line. A value obtained by integrating values inside the solid or dot- and dash-line is the total temperature of electrons. The intensity of the emission spectrum of plasma has a correlation relative to electron temperature.

Figure 2:
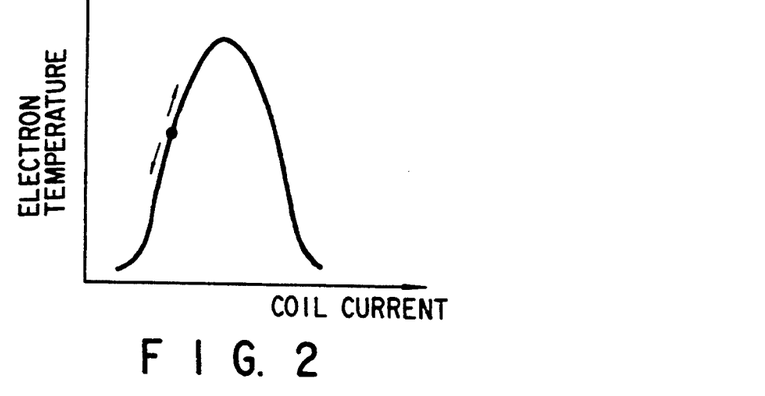
FIG. 2 is a characteristic view showing how coil current is related to average electron temperature of plasma in the case of the apparatus shown in FIG. 1.

FIG. 2 shows how the average electron temperature is related to current applied to the coils 44 and 54 to adjust the intensity of magnetic field. In FIG. 2, the abscissa represents coil current while the ordinate electron temperatures. As apparent from FIG. 2, the characteristic curve denotes the distribution of gausses having a peak at the time when microwave is coupled with electrons (or when the frequency of microwave resonates with the cyclotron movement of electrons dependent upon the intensity of magnetic field). When the value of coil current is changed, therefore, the electron temperature can be controlled to keep the state of plasma certain.

Figure 3A:
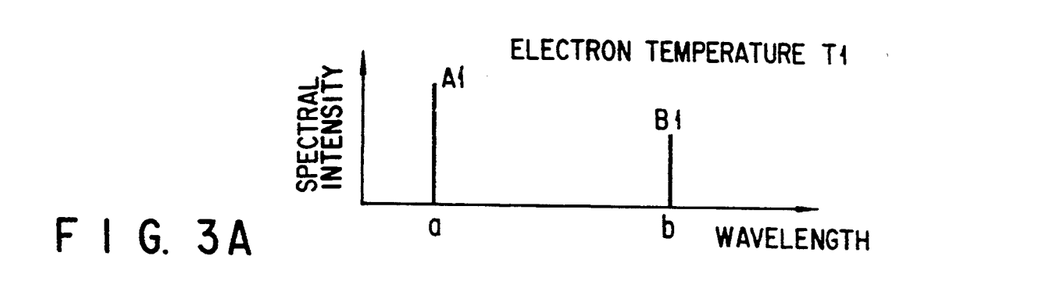
FIGS. 3A through 3C are characteristic views showing how intensities of Ar atom spectra having two different wavelengths are changed when the electron temperature changes.
Figure 3B:
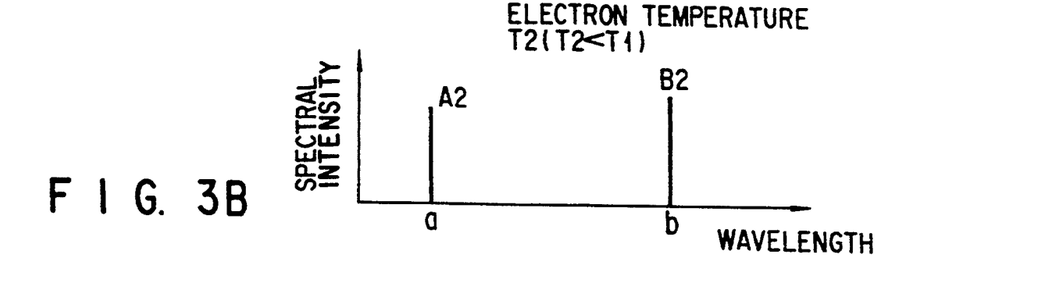
Figure 3C:
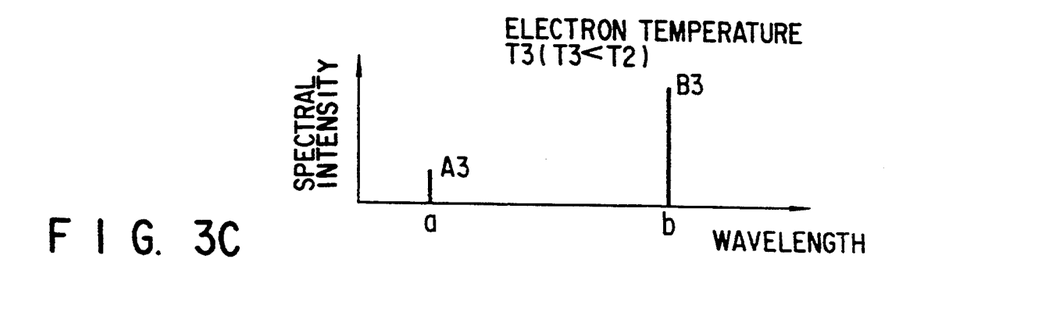

FIGS. 3A through 3C show characteristics of two spectral intensities of argon (Ar) atoms having different wavelengths. They were obtained by dispersing the light emitted from the plasma of mixed gas of HBr, $Cl_2$ and Ar, and measuring them under different electron temperatures. The spectrum having a relatively short wavelength (a) represents that of Ar ions and the spectrum having a relatively long wavelength (b) that of Ar radicals. As apparent from FIGS. 3A through 3C, the spectral intensities become different depending upon the electron temperature. The spectral intensity of the short wavelength (a) becomes larger as the electron temperature rises higher. The spectral intensity of the long wavelength (b), however, becomes smaller as the electron temperature rises higher.

Spectral intensities of wavelengths (a) and (b) are applied from the first and second spectroscopes 64 and 66 to the CPU 70. When the state of plasma is kept certain under such a state that the electron temperature equals to $T_2$ as shown in FIG. 3B, for example, the relation of spectral intensities $A_2$ and $B_2$ of wavelengths (a) and (b), such as the rate of $A_2$ relative to $B_2$, is stored, as a reference value, in the memory of the CPU 70.

When spectral intensities of wavelengths (a) and (b) derived from the plasma which is under observation are $A_1$ and $B_1$ as shown in FIG. 3A, the rate of $A_1/B_1$ becomes larger than that of $A_2/B_2$ stored. This shown that an electron temperature $T_1$ of the plasma is higher than the temperature $T_2$ set. When the electron temperature is controlled using a left part of the characteristic curve shown in FIG. 2, therefore, the electron temperature of the plasma can be lowered by making the value of coil current smaller.

When spectral intensities of wavelengths (a) and (b) derived from the plasma are $A_3$ and $B_3$ as shown in FIG. 3C, however, the rate of $A_3/B_3$ becomes smaller than that of $A_2/B_2$ stored. This shows that the electron temperature $T_1$ of the plasma is lower than the temperature $T_2$ set. When the electron temperature is controlled using the left part of the characteristic curve shown in FIG. 2 as described above, the electron temperature of the plasma can be raised by making the value of coil current larger.

Two spectra of Ar ions or radicals, for example, can be selected as those of Ar atoms having two different wavelengths.

According to the above-described embodiment, the value of coil current added to the coils 44 and 46 is controlled so as to keep constant the ratio of spectral intensities of different two wavelengths obtained by dispersing the light emitted from plasma. The electron temperature of plasma can be thus made substantially certain. In short, one element of the state of plasma can be kept certain. Particularly, Ar atoms add nothing to the chemical etching from the beginning of etching process to the ending thereof. This enables the plasma control to be achieved with less wrong detection but with a higher reliability.

Atoms which are independent of the progress of etching are not limited to those obtained from carrier gas. Monitoring gas may be introduced to monitor its spectra emitted from plasma. Further, instead of argon gas used in the method described above, helium gas or nitrogen gas may be used as carrier gas or monitoring gas.

The control to make the state of plasma certain can also be achieved by changing parameters other than coil current. Particularly in the case of the ECR etching apparatus, however, the easiest and most stable method of controlling the state of plasma is to change coil current. This is because magnetic field is related to the coupling of microwave and electrons in the electron cyclotron resonance and because microwave and electrons can be made either coupled or not by changing the intensity of magnetic field. When microwave and electrons are made coupled or nearly coupled, the electron temperature becomes high but when they are made remote from their being coupled, it becomes low. To control the state of plasma by controlling the electron temperature, therefore, it it the easiest method that coil current added to the coils 44 and 54 which form the magnetic field generator means is changed.

The above-described method is intended to make the state of plasma certain, but the state of plasma can also be made optimum by using the feedback control. As an example of this, the amount of ions and radicals generated in the chamber 10 is controlled to create the optimum etching condition. Generally, ions are more easily generated and excited as the electron temperature becomes higher, and the amount of ions is thus increased in the chamber 10. When the electron temperature is made low, however, the amount of radicals generated becomes larger as compared with the amount of ions generated. When the amount of ions or radicals generated is changed in this manner, the optimum etching can be achieved. Therefore, etching is carried out, while reducing the amount of ions generated, in order to prevent the wafer from being damaged when the etching process is coming to end. The value of coil current is controlled, for example, from the beginning of the etching process to the end point thereof to obtain the electron temperature $T_2$ shown in FIG. 3B, and after the end point of the etching process is detected, coil current is adjusted to obtain an electron temperature $T_3$ shown in FIG. 3C so as to prevent the wafer from being damaged. The optimum etching condition can also be created when the amount of ions or radicals generated is adjusted on the basis of coil current and depending on characteristics of etching gases and materials used or etching isotropy and anisotropy needed.

Figure 8:
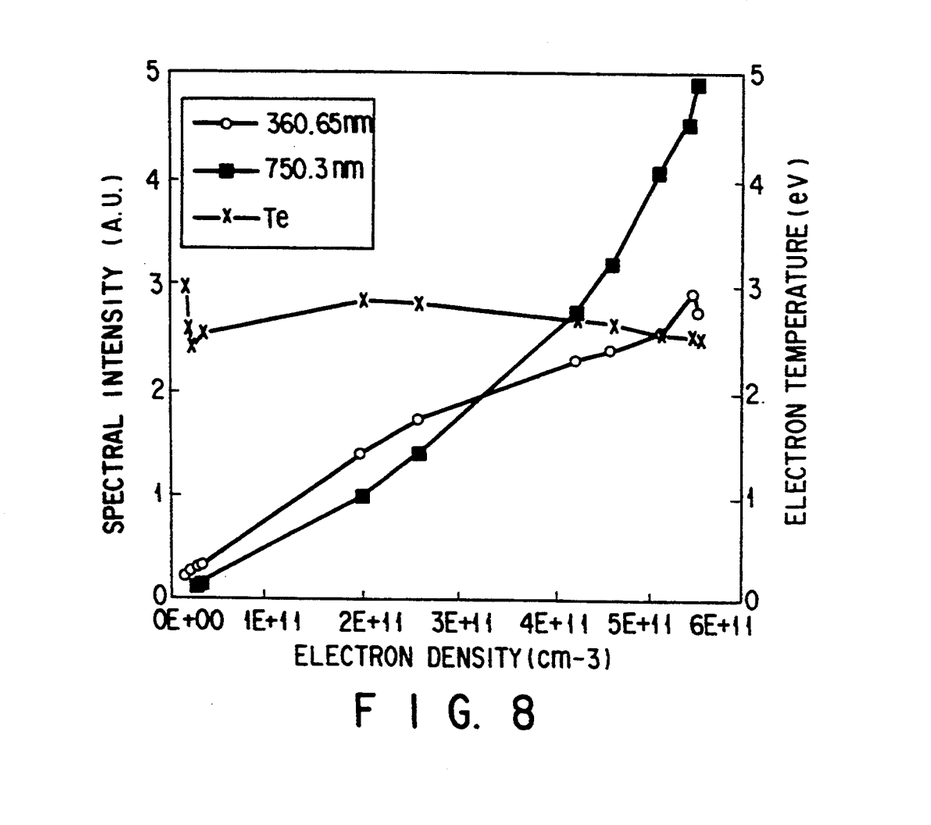
FIG. 8 shows how the electron density of plasma is related to both of Ar atom spectra and electron temperature in the case of the apparatus shown in FIG. 1.

FIG. 8 is a graph showing how electron density, which is another element for defining the state of plasma, is related to spectra of Ar atoms and to the electron temperature of the plasma generated by the above-described apparatus according to the above-described manner.

The electron density was changed in this case by adjusting microwave power. The electron density was low when microwave power added was small, but it was increased more and more as microwave power added was made larger. The electron temperature, however, was left almost unchanged even when microwave power added was changed. Spectra of Ar atoms obtained by dispersing the light emitted from the plasma and having wavelengths of 360.65 nm and 750 nm were selected. Both of these spectra increased their intensities as the electron density was increased.

Close relations exist, as described above, between microwave power and electron densities and between electron densities and spectral intensities. Therefore, microwave power can be adjusted on the basis of information obtained by monitoring spectral intensities in order to obtain a predetermined electron density. More specifically, data relating to the above-mentioned relations of spectra selected are previously provided and stored in the memory of the CPU 70. As shown FIG. 8, for example, a spectrum of relatively long wavelength depends more highly on the electron density as compared with the one of relatively short wavelength. Therefore, the spectral intensity ratio of both spectra relative to microwave power added can be used as control data. The light emitted from the plasma is dispersed and intensities of spectra selected are measured during the etching process. The electron density of the plasma then created is calculated from measured values by the CPU 70 and microwave power is adjusted to bring the calculated electron density nearer to a predetermined one.

A second embodiment of the present invention applied to the etching apparatus provided with parallel plates, particularly to the reactive ion etching apparatus will be described with reference to FIG. 4.

Figure 4:
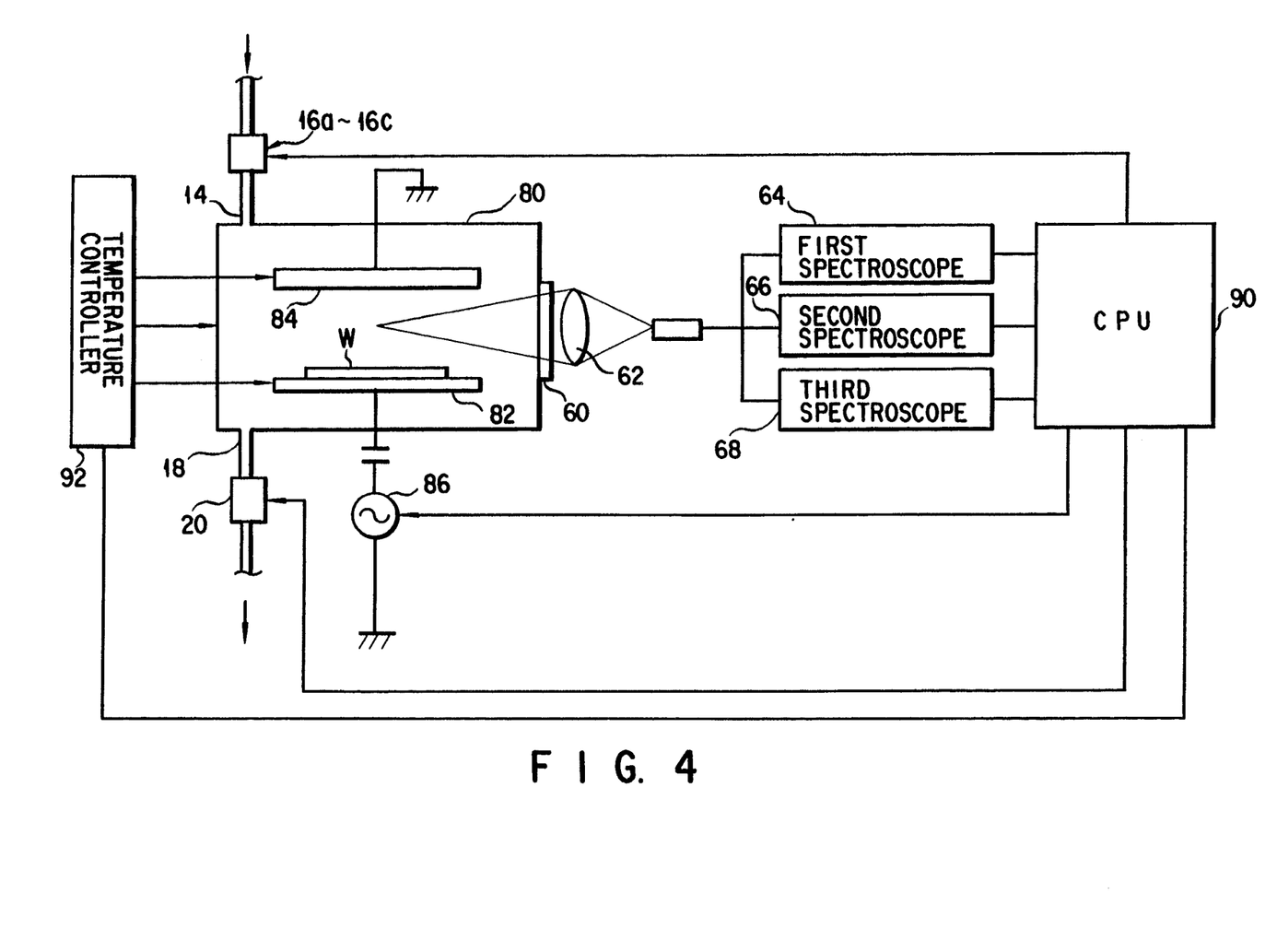
FIG. 4 schematically shows the reactive ion etching apparatus according to a second embodiment of the present invention.

In FIG. 4, an electrode 82 on which a semiconductor wafer W is mounted and another electrode 84 which is opposed to the electrode 82 are arranged in a process chamber 80. RF power source 86 is connected to the wafer-mounted electrode 82 while the opposed electrode 84 is earthed. As seen in the case of the first embodiment, the light emitted from plasma is guided to the first and second spectroscopes 64 and 66 through the detection window 60 and the lens 62 to monitor the state of plasma.

A CPU 90 serves as means for controlling the state of plasma, and various kinds of parameter, by which the state of plasma can be changed, can be changed. For example, RF power can be adjusted by the RF power source 86 and the wall temperature of the chamber 80 and temperatures of electrodes 82 and 84 can also be adjusted. The CPU 90 is connected to the RF power source 86 and a temperature controller 92 for this purpose. In addition, the CPU 90 can adjust vacuum degree of the chamber 80. The mass flow controllers 16a-16c which are connected to the gas pipe 14 to adjust flow rates of gases and the pressure controller 20 which is connected to the exhaust pipe 18 are therefore controlled by the CPU 90.

When the above-described apparatus is to be used, the wafer W is mounted on the electrode 82 in the chamber 80 and the chamber 80 is set to have a predetermined vacuum atmosphere. Etching gas such as $CHF_3$, for example, is then introduced into the chamber 80 while exhausting the chamber 80. When RF power is added to the electrode 82 under this state, the gas is made into plasma. The wafer W on the electrode 82 is thus etched by the chemical action of radicals of etching gas atoms in the plasma and by the physical action of ions in the plasma.

The relation of pressure in the chamber 80 relative to the spectral intensity of hydrogen, which is obtained by dispersing the light emitted from the plasma generated from etching gas $CHF_3$, will be described referring to FIGS. 5 and 6. Pressure in the chamber was changed in a range of 10 mTorr-200 mTorr while the flow rate of $CHF_3$ introduced was set 50 sccm, and RF power was set 600 W. Plasma was thus generated.

Figure 5:
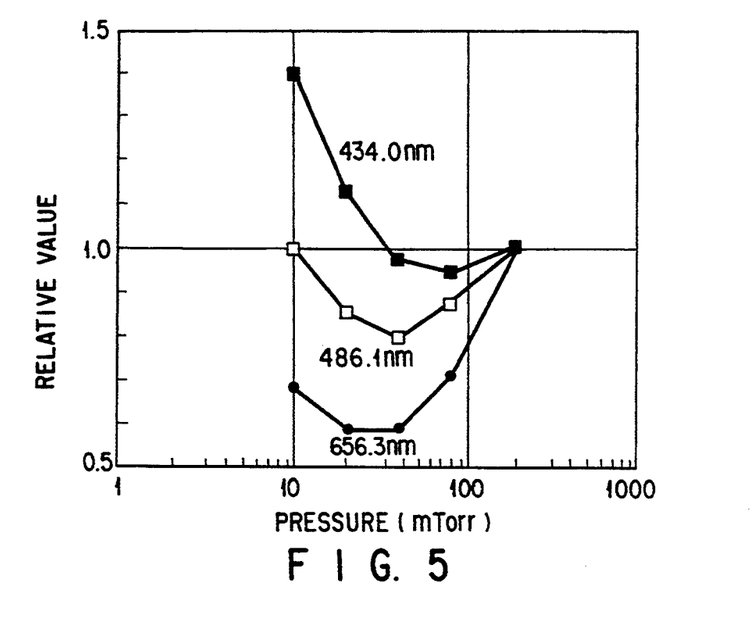
FIG. 5 is a characteristic view showing the pressure-depending characteristics of those relative intensities of hydrogen atom spectra which have three different wavelengths, each relative intensity having a reference value 1.0 which represents intensity when a pressure is 200 Torr.

FIG. 5 shows relative emission light intensities of spectra of hydrogen atom H obtained by dispersing the emission light of the plasma and having three different wavelengths of 434.0 nm, 486.1 nm and 656.3 nm. Each relative intensity has a reference value 1.0 which represents the spectral intensity of each wavelength when the pressure in the chamber 80 is 200 mTorr.

Figure 6:
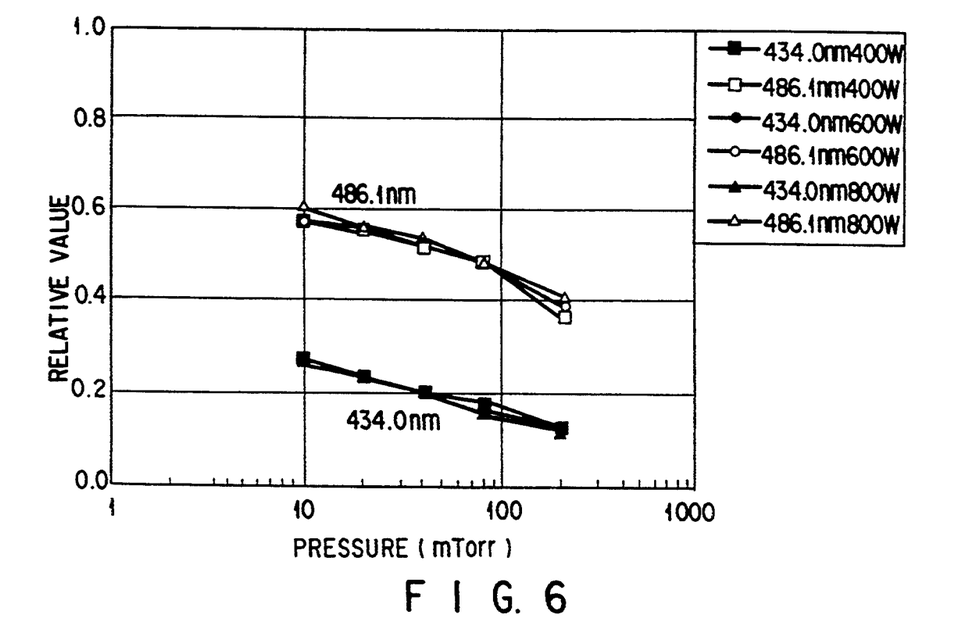
FIG. 6 is a characteristic view showing how the intensity ratios of spectra of 434.0 nm and 486.1 nm to a spectrum of 656.3 nm are related to pressure and RF power.

FIG. 6 shows pressure-depending characteristics of intensity ratios of spectra having two wavelengths of 434.0 nm and 486.1 nm to a spectrum having a wavelength of 656.3 nm. As described above, these three spectra were obtained by dispersing the emission light of the plasma and represent hydrogen atom H. Each emission light spectral intensity was measured while changing RF power to 400 W, 600 W and 800 W. It can be understood from FIG. 6 that the intensity ratios of 434.0 nm and 486.1 nm to 656.3 nm increase as vacuum degree becomes higher. It is also apparent that the pressure-depending characteristics of the above-mentioned ratios are left almost unchanged even if RF power is changed.

The spectral intensity of each wavelength depends upon the energy level of electrons which surround the atomic nucleus. This energy level is generally denoted by the value of n. The emission light of 656.3 nm, for example, is caused when the energy level is changed from $n=3$ to $n=2$. The emission light of 486.1 nm is caused when the energy level is changed from $n=4$ to $n=2$. Further, the emission light of 434.0 nm is caused when the energy level is changed from $n=5$ to $n=2$. When spectral intensities of three wavelengths are related to one another, therefore, it can be confirmed what a value the energy level of hydrogen atom in plasma has.

As apparent from FIGS. 5 and 6, the spectral intensity of hydrogen atom changes depending upon the pressure (or vacuum degree) in the chamber 80. When the pressure is decreased or the vacuum degree is increased, the electron temperature of plasma is raised. When the pressure is increased or the vacuum degree is decreased, the electron temperature of plasma is lowered. Although coil current which is used to adjust magnetic field has been changed to control the state of plasma in the case of the ECR plasma etching apparatus with which the first method of the present invention is carried out, the vacuum degree of the chamber 80 is changed, while relating plural different spectral intensities to one another, to similarly control the state of plasma in the case of the reactive ion etching apparatus with which this method of the present invention is conducted.

According to the present invention, intensities of spectra obtained by dispersing the emission light of plasma and having plural different wavelengths are detected and the state of plasma can be confirmed from the relation, such as ratio, of these detected intensities as described above. The state of plasma can be kept certain or optimum by adjusting the pressure or vacuum degree in the chamber 80. Particularly, where hydrogen atom adds nothing to the chemical etching from the beginning of etching process to the ending thereof, it is possible to achieve the plasma control with less wrong detection but with a higher reliability. In addition, the state of plasma can also be controlled by changing one of plasma generating parameters other than the pressure in the chamber.

According to the present invention as described above, any influence of noises and variations can be removed from detected information when plural or two different spectra are used. Therefore, the state of plasma can be controlled from the detected information with a higher reliability.

It should be understood that the present invention is not limited to the above-described embodiments but that various changes and variations can be made without departing from the spirit and scope of the present invention. The present invention can be applied to the magnetron etching apparatus as well, in which crossing electric and magnetic fields are formed to generate plasma. It can also be applied to the plasma processing apparatuses such as the plasma CVD apparatus. Further, systems for moving the focus of that lens through which the emission light of plasma is collected, and for adjusting the temperature of the detection window not to cause any film to adhere to the window may be added to more correctly monitor the state of plasma.

What is claimed is:

1. A method of generating plasma for processing a substrate therewith in a process chamber, comprising the steps of:

selecting a plasma to be generated in said process chamber and raw gas for generating said plasma selected;

selecting a first parameter upon which a generation of said plasma depends, an electron temperature of said plasma being alterable by changing said first parameter;

generating control data as a function of intensities of spectra of light emitted from said plasma having first and second wavelengths, and establishing, as a first datum, a relationship between said control data and said electron temperature of said plasma;

establishing, as a second datum, a relationship between said electron temperature of said plasma and said first parameter;

establishing, as a third datum, a relationship between said control data and said first parameter of said first datum, and storing said third datum in a memory of a control unit;

storing a selected value of said control data in said memory of said control unit;

loading said substrate into said process chamber;

establishing a vacuum atmospheric condition within said process chamber;

introducing said raw gas into said process chamber while exhausting said process chamber;

generating plasma by forming said raw gas into generated plasma;

guiding light emitted from said generated plasma into first and second spectroscopes;

detecting intensities of spectra of said light emitted from said generated plasma having said first and second wavelengths via said first and second spectroscopes;

calculating a present value of said control data from detected spectral intensities of light emitted from said generated plasma by means of said control unit;

adjusting said first parameter via said control unit while monitoring said present value of said control data such that said present value becomes closer to said selected value of said control data over time; and processing said substrate with said generated plasma, wherein each of said spectra of said light emitted from said generated plasma having said first or second wavelengths represents a first atom or molecule which neither substantially nor chemically acts on said substrate when said substrate is being processed, wherein said control data represents a ratio of an intensity of light emitted from said generated plasma having said first wavelength to an intensity of light emitted from said generated plasma having said second wavelength, and wherein said generated plasma is excited by electron cyclotron resonance.

2. The method according to claim 1, wherein said electron cyclotron resonance is caused by a magnetic field generated within said process chamber and microwaves introduced into said process chamber.

3. The method according to claim 2, wherein said first parameter represents an intensity of said magnetic field.

4. The method according to claim 2, wherein said raw gas includes gas containing atoms which enhance a chemical etching action on said substrate.

5. The method according to claim 4, wherein said first atom or molecule is selected from a group consisting of argon, helium, and nitrogen.

6. The method according to claim 4, wherein said first atom or molecule is hydrogen.

7. The method according to claim 4, wherein said raw gas comprises said first atom or molecule and serves as a monitoring gas for monitoring spectra of light emitted from said generated plasma.

8. A method of generating plasma for processing a substrate therewith in a process chamber, comprising the steps of:

selecting a plasma to be generated in said process chamber and raw gas for generating said plasma selected;

selecting a first parameter upon which a generation of said plasma depends, an electron temperature of said selected plasma being alterable by changing said first parameter;

generating control data as a function of intensities of spectra of light emitted from said plasma having first and second wavelengths, and establishing, as a first datum, a relationship between said control data and said electron temperature of said plasma;

establishing, as a second datum, a relationship between said electron temperature of said plasma and said first parameter;

establishing, as a third datum, a relationship between said control data and said first parameter of said first datum, and storing said third datum in a memory of a control unit;

storing a selected value of said control data in said memory of said control unit;

loading said substrate into said process chamber;

establishing a vacuum atmospheric condition within said process chamber;

introducing said raw gas into said process chamber while exhausted said process chamber;

generating plasma by forming said raw gas into generated plasma;

guiding light emitted from said generated plasma into first and second spectroscopes;

detecting intensities of spectra of said light emitted from said generated plasma having said first and second wavelengths via said first and second spectroscopes;

calculating a present value of said control data from detected spectral intensities of light emitted from said generated plasma by means of said control unit;

adjusting said first parameter via said control unit while monitoring said present value of said control data such that said present value becomes closer to said selected value of said control data over time; and processing said substrate with said generated plasma, wherein each of said spectra of said light emitted from said generated plasma having first said first or second wavelengths represents a first atom or molecule which neither substantially nor chemically acts on said substrate when said substrate is being processed, wherein said control data represents a ratio of an intensity of light emitted from said generated plasma having said first wavelength to an intensity of light emitted from said generated plasma having said second wavelength, and wherein said plasma is excited by a high-frequency electric field generated between parallel plate electrodes within said process chamber.

9. The method according to claim 8, wherein said first parameter represents a pressure within said process chamber.

10. The method according to claim 8, wherein said raw gas includes gas containing atoms which enhance a chemical etching action on said substrate.

11. The method according to claim 10, wherein said first atom or molecule is selected from a group consisting of argon, helium, and nitrogen.

12. The method according to claim 10, wherein said first atom or molecule is hydrogen.

13. The method according to claim 10, wherein said raw gas comprises said first atom or molecule and serves as a monitoring gas for monitoring spectra of light emitted from said generated plasma.

14. A method of generating plasma for processing a substrate therewith in a process chamber, comprising the steps of:

selecting a plasma to be generated in said process chamber and raw gas for generating said plasma selected;

selecting a first parameter upon which a generation of said plasma depends, an electron density of said plasma being alterable by changing said first parameter;

generating control data as a function of intensities of spectra of light emitted from said plasma having first and second wavelengths, and establishing, as a first datum, a relationship between said control data and said electron density of said plasma;

establishing, as a second datum, a relationship between said control data and said electron density of said plasma;

establishing, as a third datum, a relationship between said control data and said first parameter of said first datum, and storing said third datum in a memory of a control unit;

storing a selected value of said control data in a memory of said control unit;

loading said substrate into said process chamber;

establishing a vacuum atmospheric condition within said process chamber;

introducing said raw gas into said process chamber while exhausting said process chamber;

generating plasma by forming said raw gas into generated plasma;

guiding light emitted from said generated plasma into first and second spectroscopes;

detecting intensities of spectra of said light emitted from said generated plasma having said first and second wavelengths via said first and second spectroscopes;

calculating a present value of said control data from detected spectral intensities of light emitted from said generated plasma by means of said control unit;

adjusting said first parameter via said control unit by monitoring said present value of said control data such that said present value becomes closer to said selected value of control data over time; and processing said substrate with said generated plasma, wherein each of said spectra of said light emitted from said generated plasma having said first or second wavelengths represents a first atom or molecule which neither substantially nor chemically acts on said substrate when said substrate is being processed, wherein said control data represents a ratio of an intensity of light emitted from said generated plasma having said first wavelength to an intensity of light emitted from said generated plasma having said second wavelength, and wherein said generated plasma is excited by electron cyclotron resonance.

15. The method according to claim 14, wherein said electron cyclotron resonance is caused by a magnetic field generated within said process chamber and microwaves introduced into said process chamber.

16. The method according to claim 15, wherein said first parameter represents an intensity of said microwaves.

17. The method according to claim 15, wherein said raw gas includes gas containing atoms which enhance a chemical etching action on said substrate.

18. The method according to claim 17, wherein said first atom or molecule is selected from a group consisting of argon, helium, and nitrogen.

* * * * *